(12) United States Patent
Czarnotta et al.

(10) Patent No.: US 8,577,122 B2
(45) Date of Patent: Nov. 5, 2013

(54) METHOD AND DEVICE FOR TESTING CIGARETTE PACKAGES WRAPPED WITH FILM

(75) Inventors: Michael Czarnotta, Bremen (DE); Vincent Kral, Bremen (DE); Dirk Drücke, Bremen (DE)

(73) Assignee: Focke & Co. (GmbH & Co. KG), Verden (DE)

( * ) Notice: Subject to any disclaimer, the term of this patent is extended or adjusted under 35 U.S.C. 154(b) by 451 days.

(21) Appl. No.: 12/988,080

(22) PCT Filed: Apr. 6, 2009

(86) PCT No.: PCT/EP2009/002521
§ 371 (c)(1),
(2), (4) Date: Oct. 15, 2010

(87) PCT Pub. No.: WO2009/132752
PCT Pub. Date: Nov. 5, 2009

(65) Prior Publication Data
US 2011/0038526 A1    Feb. 17, 2011

(30) Foreign Application Priority Data
Apr. 28, 2008  (DE) .................. 10 2008 021 199

(51) Int. Cl.
*G06K 9/00* (2006.01)

(52) U.S. Cl.
USPC .................................. 382/143; 382/141

(58) Field of Classification Search
USPC ................... 382/141, 143; 209/509, 734
See application file for complete search history.

(56) References Cited

U.S. PATENT DOCUMENTS

| | | | | |
|---|---|---|---|---|
| 5,734,742 | A * | 3/1998 | Asaeda et al. | 382/141 |
| 2002/0118873 | A1 * | 8/2002 | Tran et al. | 382/143 |

(Continued)

FOREIGN PATENT DOCUMENTS

| | | |
|---|---|---|
| DE | 2414034 | 10/1974 |
| EP | 0278577 | 8/1988 |

(Continued)

OTHER PUBLICATIONS

Machine Translation of Naito (JP 2002-214150).*

(Continued)

*Primary Examiner* — Edward Park
(74) *Attorney, Agent, or Firm* — Laurence P. Colton; Smith Risley Tempel Santos LLC

(57) ABSTRACT

A method for testing moving products having at least two layers, such as cigarette packages wrapped with film, wherein at least one layer of the product, namely an inner layer which is arranged further inwards, is covered at least regionally by at least one, at least partially transparent product layer, namely an outer layer which is arranged further outwards, wherein the outer layer of the product is illuminated under an angle of incidence of about 35°, with light, in which the light that is reflected at this layer comprises at least 70%, at least 90%, or at least 95%, of linearly s-polarized light, the s-polarized component of the light reflected by the outer layer and/or of the light reflected by the inner layer and/or the p-polarized component of the light reflected by the outer layer and/or of the light reflected by the inner layer are recorded in each case using at least one suitable electrooptic recording element in the form of an image or partial image of the product and wherein the recorded s-polarized and/or the recorded p-polarized light component are evaluated in order to be able to draw conclusions relating to features of the outer layer and/or of the inner layer.

21 Claims, 3 Drawing Sheets

(56) References Cited

U.S. PATENT DOCUMENTS

2006/0262297 A1* 11/2006 Matsui et al. ............. 356/237.5
2008/0292780 A1* 11/2008 Vangheluwe et al. ............ 427/8

FOREIGN PATENT DOCUMENTS

| | | |
|---|---|---|
| EP | 0330495 | 8/1989 |
| EP | 0371550 | 6/1990 |
| EP | 0790187 | 8/1997 |
| EP | 0902275 | 3/1999 |
| EP | 1026082 | 8/2000 |
| EP | 1188674 | 3/2002 |
| EP | 1553406 | 7/2005 |
| JP | 2002-107304 A | 4/2002 |
| JP | 2002-214150 A | 7/2002 |
| JP | Hei09-269296 A | 11/2009 |

OTHER PUBLICATIONS

Machine Translation of Takei (JP 2002-107304).*
Japanese Patent Office, Official Action, Aug. 17, 2012.

* cited by examiner

METHOD AND DEVICE FOR TESTING CIGARETTE PACKAGES WRAPPED WITH FILM

STATEMENT OF RELATED APPLICATIONS

This application is the Patent Cooperation Treaty (PCT) Chapter II National Phase of and claims the benefit of PCT International Application No. PCT/EP2009/002521 having an International Filing Date of 6 Apr. 2009, which in turn claims priority on German Patent Application No. 10 2008 021 199.0 having a filing date of 28 Apr. 2008.

BACKGROUND OF THE INVENTION

1. Technical Field

The present invention relates to a method for testing preferably moving products having at least two layers, in particular packages wrapped with film, preferably cigarette packages, wherein at least one layer of the product, which is arranged further inwards,—the inner layer—, is covered at least regionally by at least one, at least partially transparent product layer, which is arranged further outwards,—the outer layer. The invention further relates to a device for testing such products.

2. Prior Art

Cigarette packages are typically provided at the end of manufacture with labels, coupons or other cut blanks. Subsequently they are wrapped with a transparent film. Automated optical testing of the cigarette package, in particular of said cut blanks, for defects is extremely difficult once the package has been wrapped with film. This is because reflections from the film interfere with the optical tests, for example by means of a camera.

It can also be difficult to carry out an automated optical test of the film itself. This is because images of the film, recorded by cameras, are superposed by images of the cigarette package situated under the film.

BRIEF SUMMARY OF THE INVENTION

The invention is therefore based on the object of specifying an automated optical method for testing products of the type mentioned in the introduction, in particular for cigarette packages which are wrapped with film, in which both layers of the products can be tested as reliably as possible. The invention is also based on the object of specifying a testing device which can be used to carry out such a method.

This object is achieved by way of a method for testing moving products having at least two layers, wherein at least one layer of the product, which is arranged further inwards, namely an inner layer, is covered at least regionally by at least one, at least partially transparent product layer, which is arranged further outwards, namely an outer layer, comprising the steps of:
  a) illuminating the outer layer of the product by unpolarized light at an angle of incidence of about 35°, with light that is reflected at the outer layer comprising at least 70% of linearly s-polarized light;
  b) the s-polarized component of the light reflected by the outer layer and/or of light reflected by the inner layer and/or a p-polarized component of the light reflected by the outer layer and/or of the light reflected by the inner layer is/are recorded in each case separately using at least one suitable electrooptic recording element in the form of an image or partial image of the product,
  c) the recorded s-polarized and/or the recorded p-polarized light component is/are evaluated in order to be able to draw conclusions relating to features of the outer layer and/or of the inner layer.

The object is furthermore achieved by way of a device for testing moving products having at least two layers, wherein at least one layer of the product, which is arranged further inwards, namely an inner layer, is covered at least regionally by at least one, at least partially transparent product layer, which is arranged further outwards, namely an outer layer, wherein the device has at least one illumination element and at least one electrooptic recording element, and wherein:
  a) the illumination element is directed at least at one side of the product such that unpolarized light emitted by the illumination element illuminates the outer layer of the product under an angle of incidence of about 35°, with light comprising at least 70% of linearly s-polarized light,
  b) a polarization filter for filtering p-polarized light and/or a polarization filter for filtering the s-polarized light is/are arranged in a beam path of the light reflected at the outer layer and/or the inner layer,
  c) the at least one electrooptic recording element is positioned such that it records the s-polarized light and/or the p-polarized light after passage through the polarization filter(s) in each case separately as an image or partial image of the product.

The method according to the invention is accordingly characterized in that that layer of the product that is arranged further outwards and is at least partially transparent to light is illuminated by light at an angle of incidence, preferably almost 35°, with the light that is reflected at this layer comprising at least 70%, preferably at least 90%, especially preferably at least 95%, of linearly s-polarized light.

The s-polarized component of the light reflected by that layer that is arranged further outwards and/or of the light reflected by that layer that is arranged further inwards and/or the p-polarized component of the light reflected by that layer that is arranged further outwards and/or of the light reflected by that layer that is arranged further inwards is/are recorded in each case using at least one suitable electrooptic recording element or a light detector—camera—in the form of an image or partial image of the product.

The recorded s-polarized and/or the recorded p-polarized light component(s) is/are then evaluated in order to be able to draw conclusions relating to features of that layer that is arranged further outwards and/or of that layer that is arranged further inwards, especially in terms of intactness and/or in terms of correct positioning of that layer that is arranged further outwards and/or of that layer that is arranged further inwards.

As far as that layer that is arranged further inwards and that layer that is arranged further outwards are concerned, they can be interconnected or not. In particular, they can be arranged such that they lie next to or on top of each other with or without a mutual spacing. What is important is that that layer that is arranged further outwards is at least partially transparent to visible light. The material, of which that layer that is arranged further inwards is made from, preferably differs from that layer that is arranged further outwards. That layer that is arranged further outwards will be referred to below in brief as the outer layer, and that layer that is arranged further inwards as the inner layer. The outer layer can in this case of course also be the outermost layer of the product, but does not have to be.

The invention proceeds from the finding that transparent or at least partially transparent outer layers of products, such as cigarette packages wrapped in film, linearly polarizes light that is irradiated under the so-called Brewster angle. In other words, in this case the light that is reflected by the outer layer to be tested—for example the film—is s-polarized, i.e. polarized at right angles to the plane of incidence of the light.

As regards the light with which the product is illuminated, said light is preferably unpolarized. However, it is theoretically also conceivable for circularly polarized light to be irradiated instead of unpolarized light.

If the light is incident exactly at the Brewster angle—in conventional films about 35°—, nearly or exactly 100% of the light that is reflected by the outer layer is s-polarized. On the other hand, that part of the light that passes through the film and is refracted according to the known laws of refraction, strikes the inner layer of the product to be tested, for example a corresponding area of the cigarette package. This can be the surface of a package wall, the label, a coupon or the like. There, the light is partially absorbed and partially reflected. The light reflected by the inner layer is at least predominantly p-polarized, i.e. polarized parallel to the plane of incidence of the light.

According to the invention, the stated relationships are used in order to optically separate the outer layer and the inner layer from each other. This is because the p-polarized light component from all the light reflected by the inner layer and by the outer layer originates at least predominantly, preferably completely, from the inner layer. Due to the recording of the p-polarized light component from all the reflected light, interfering light components, which originate from the at least partially transparent outer layer and which are at least predominantly, preferably completely, s-polarized, can therefore be faded out.

Conversely, due to the recording of only s-polarized light components of the reflected light, reflections from the inner layer, that is to say the cigarette package, can be at least partially faded out. This is because the light components, which originate from the inner layer, are at least predominantly p-polarized.

In one preferred embodiment of the invention, in which the outer layer is part of the film wrap of a cigarette package and the inner layer is part of the cigarette package, in particular a label, a coupon, a package wall or the like, the angle of incidence, under which the outer layer is illuminated, is greater than 85% of the Brewster angle of the outer layer and smaller than 115% of the Brewster angle of the outer layer.

A test device for carrying out the method according to the invention has, in addition to the at least one electrooptic recording element—camera—an illumination element. Here, the illumination element is directed at least at one side of the product such that the light emitted by the illumination element illuminates the outer layer of the product under an angle of incidence, preferably almost 35°, with light, in which the light reflected at this layer comprises at least 70%, preferably at least 90%, especially preferably at least 95%, of linear s-polarized light. A polarization filter for filtering the p-polarized light and/or a polarization filter for filtering the s-polarized light is/are arranged in the beam path of the light reflected at the outer layer and/or the inner layer. The at least one camera is positioned such that it records the s-polarized light and/or the p-polarized light after passage through the polarization filter(s) in each case separately as an image or partial image of the product. At least two cameras are preferably present.

BRIEF DESCRIPTION OF THE DRAWINGS

Further particulars of the invention can be gathered from the appended claims, from the following description of preferred exemplary embodiments and from the appended drawings, in which:

DETAILED DESCRIPTION OF PREFERRED EMBODIMENTS

Figure 1:
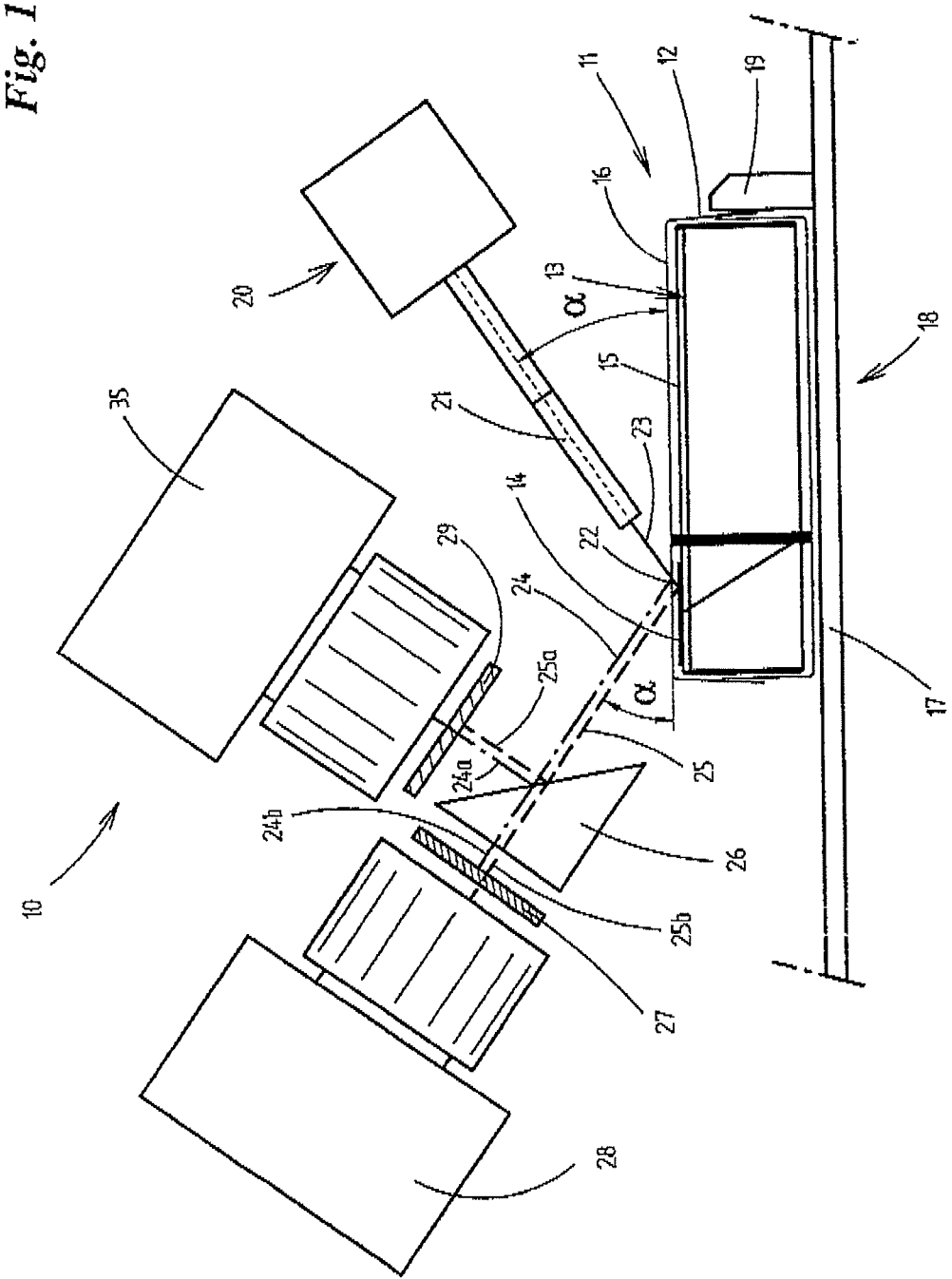
FIG. 1 shows a schematic sectional view of a test device according to the invention.

FIG. 1 shows a test device 10, with which products 11 can be tested in association with an automated, essentially optical method. The product 11 is a cigarette package 13 wrapped with a film 12. The film 12 is substantially transparent to visible light.

During the test process, the test device 10 tests a layer of the product 11 that is arranged further outwards—outer layer—, specifically the film front side 16 arranged above the front wall 15 of the cigarette package 13.

The test device 10 also tests a layer that is arranged further inwards—inner layer—of the product 11, specifically a label 14 arranged at the front wall 15, which label is naturally likewise covered by the film 12, specifically by the film front side 16.

During the test process, the product 11, that is to say the cigarette package 13 wrapped with the film 12, is moved underneath the test device 10 past the latter. For this purpose, the cigarette package 13 wrapped with the film 12 is located on a conveying run 17 of a conveyor 18 (not illustrated in more detail) of a cigarette packaging machine (likewise not illustrated). A pusher dog 19 of the conveying run 17 bears against the bottom side of the cigarette package 13 wrapped with the film 12, as a result of which the package 13 is concomitantly moved when the conveying run 17 is moved to the left.

The test device 10 has an illumination element 20 with which the film front side 16 and the label 14, which is arranged thereunder, is illuminated in a strip-wise manner with unpolarized light 23. For this purpose, the illumination element 20 has a light source (not illustrated in more detail) comprising a plurality of LEDs. Any other suitable light source can naturally also be used. The light emanating from the LEDs is guided through an illumination body 21, which ensures, as an optical diffuser, a uniform illumination of an illuminated, strip-type section 22 on the film front side 16 or the label 14, which is arranged thereunder. Here, the exit end of the diffuser 21, through which the light exits in the direction of the film front side 16 or of the label 14, has a curved, specifically concave, surface 36. This concave surface 36 is used to compensate for a curvature or arch of the package 13 around its longitudinal center axis, which is associated with manufacture. In other words, distortions of the illuminated section 22 are prevented, which would otherwise occur due to the arching of the respective package 13 that is associated with manufacture.

Figure 2:
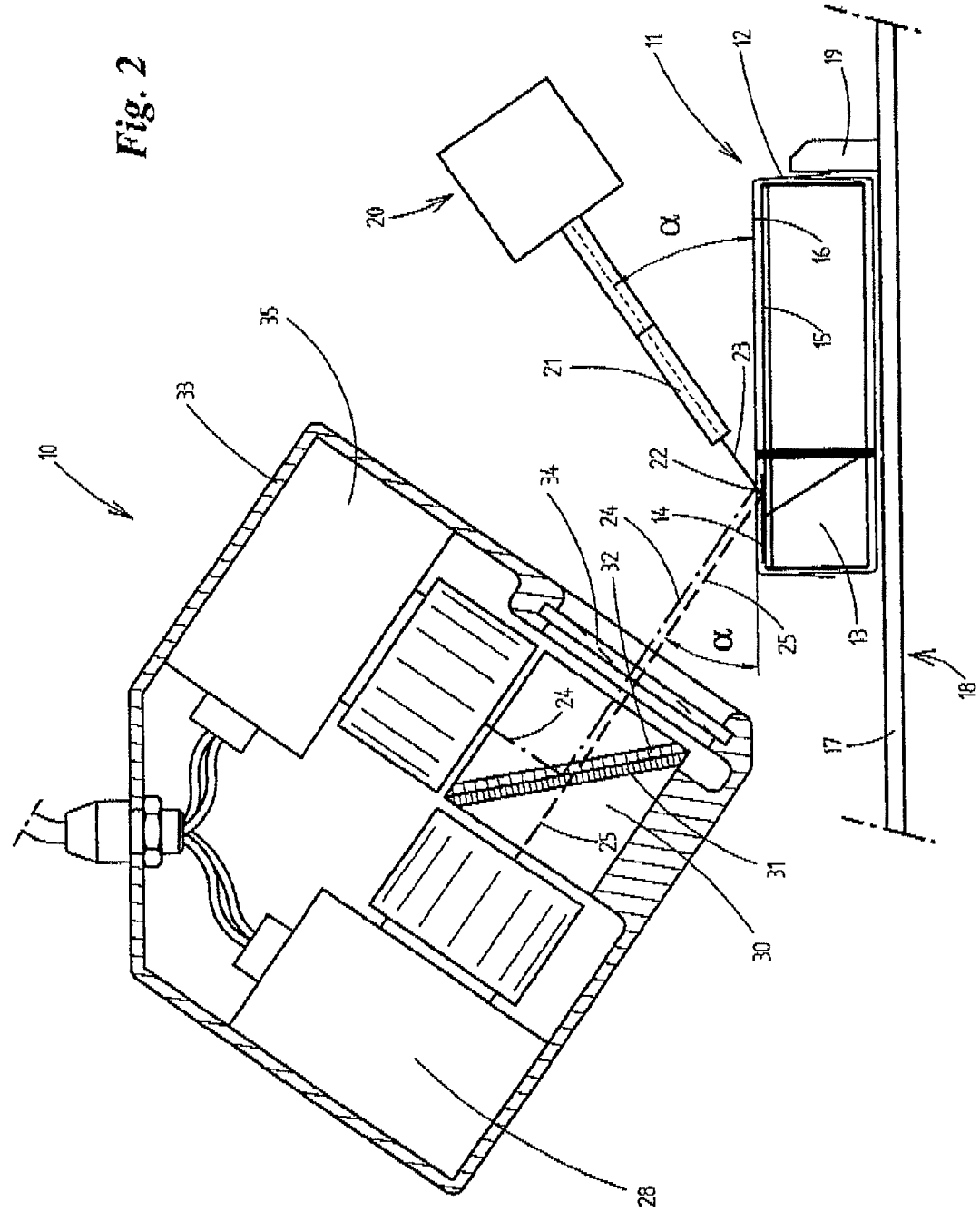
FIG. 2 shows a further embodiment of a test device according to the invention in schematic sectional view.

The illumination element 20 is here arranged above the cigarette package 13 such that the light beam 23 emitted by the illumination element 20 strikes the film front side 16 at an angle of incidence at which the light 24, which is reflected at this film front side 16, comprises at least 70%, preferably at least 90%, especially preferably 95%, of linearly s-polarized light. The angle of incidence is defined in this context as the angle between the incident beam and the perpendicular to the boundary surface or the film front side 16. In FIGS. 1 and 2, the angle of incidence is therefore 90°—α, with α being the angle between the incident beam and the boundary surface or the film front side 16.

If the light 23 strikes the film front side 16 ideally exactly at the known Brewster angle, all the light 24 reflected at the film front side 16 is linearly polarized, specifically at right angles to the plane of incidence of the light. The Brewster angle in conventional film types that are used for wrapping cigarette packages is about 35°, and thus the angle α in this case is accordingly 55°.

The following explanations of the invention are based on the assumption that the conditions are ideal as described, that is to say that the Brewster angle is observed exactly, so that all the light reflected at the film front side 16 is s-polarized. However, the invention also allows for a deviation from the exact Brewster angle, with the result that the light reflected at the film front side 16 is now only predominantly s-polarized.

The predominant component of the light 23 emanating from the illumination element 20 is typically not reflected at the film front side 16 but passes through it, is possibly refracted somewhat in the process and finally strikes the label 14.

Again a component of the light 23 striking the label 14 is then reflected at it and subsequently continues as a reflected light beam 25 nearly parallel to the s-polarized light beam 24 that is reflected at the film front side 16. The light beam 25 reflected at the label is here predominantly, although typically not completely, p-polarized, that is to say parallel to the plane of incidence.

A beam splitter 26, configured in the form of a prism, is located in the further beam path of the reflected light beams 24, 25. This beam splitter 26 splits in each case the reflected light beams 24, 25 into partial beams.

The reflected light beam 24 is here split into two partial beams 24a and 24b, with the partial beam 24a being deflected or extending at right angles to the reflected light beam 24. The partial beam 24b, on the other hand, passes through the beam splitter 26 without deflection and in a straight line. Similarly, the reflected light beam 25 is split into two partial beams 25a, 25b with corresponding paths.

A polarization filter 27, which only transmits p-polarized light but blocks s-polarized light, is located in the further beam path of the partial beams 24b, 25b, which pass through the beam splitter 26 without deflection and in a straight line.

For this reason, only that light component of the partial beam 25b that is p-polarized is allowed through the polarization filter 27 and strikes a camera 28 positioned downstream. The partial beam 24b, which is completely s-polarized, on the other hand, is blocked.

Similarly, a polarization filter 29, which only transmits s-polarized light, is arranged in the beam path of the two partial beams 24a, 25a. 100% of the completely s-polarized partial beam 24a accordingly passes through the polarization filter 29 and strikes a camera 35 positioned downstream. The partial beam 25a, however, is predominantly p-polarized and is therefore at least predominantly blocked.

As a result, the test device 10 permits the at least predominant separation of the individual light components 24, 25 from the total beam reflected by the film front side 16 and the label 14. In other words, the light components of the reflected light originating from the film front side 16 are separated from the light components originating from the label 14.

Consequently, the camera 35 records an image that is at least predominantly an image of the film front side 16, whereas the camera 28 records an image that is at least predominantly an image of the label 14. It is thus possible to optically separate film 12 and cigarette package 13 from each other.

As regards the cameras 28, 35, they are preferably line-scan cameras. The high operating speed of such cameras enables the respective images/partial images to be recorded even at high speeds of the cigarette packages 13 which are conveyed past the test device.

However, it is of course also possible in principle for the cigarette package 13 to stop for a short time during the test process so that the images of unmoving cigarette packages can be recorded.

Irrespective of this, the images recorded according to the invention are of outstanding quality and permit a particularly precise evaluation. It is possible in particular to measure features of the label 14 and features of the film front side 16 at the same time. For example, the label 14 and the film front side 16 can be tested for intactness, for the presence of minor or major defects, of color deviations, of positional deviations or the like.

For this purpose, the recorded images can be evaluated using automated processing methods known per se. To this end, the images are transmitted to a suitable evaluation apparatus, such as a computing apparatus with suitable image-processing software. The software can acquire said features by comparing the recorded images with reference images and/or by way of pattern recognition methods.

If the evaluation, for example, detects that the film front side 16 and/or the label 14 is/are defective, the cigarette package 13 in question is subsequently discharged from the production process.

As part of the evaluation, the respective image/partial image of the p-polarized light component of the reflected light recorded by the camera 28 can be subtracted from the corresponding image/partial image of the s-polarized light component recorded by the camera 35 for the purpose of examining the outer layer, specifically the film front side 16. It is possible in this manner to reduce image components originating from the label 14 which interfere with the examination of the film. This is because as mentioned above, the partial beam 25a originating from the label 14 has at least to a small extent s-polarized light components, which could accordingly pass through the polarization filter 29 and be recorded by the camera 35.

The images recorded in each case by the camera 28 and by the camera 35 can then, for example, be made to coincide using the suitable processing software and the parameters associated with each pixel, in particular brightness values, can be subtracted from each other in the manner described.

Figure 3:
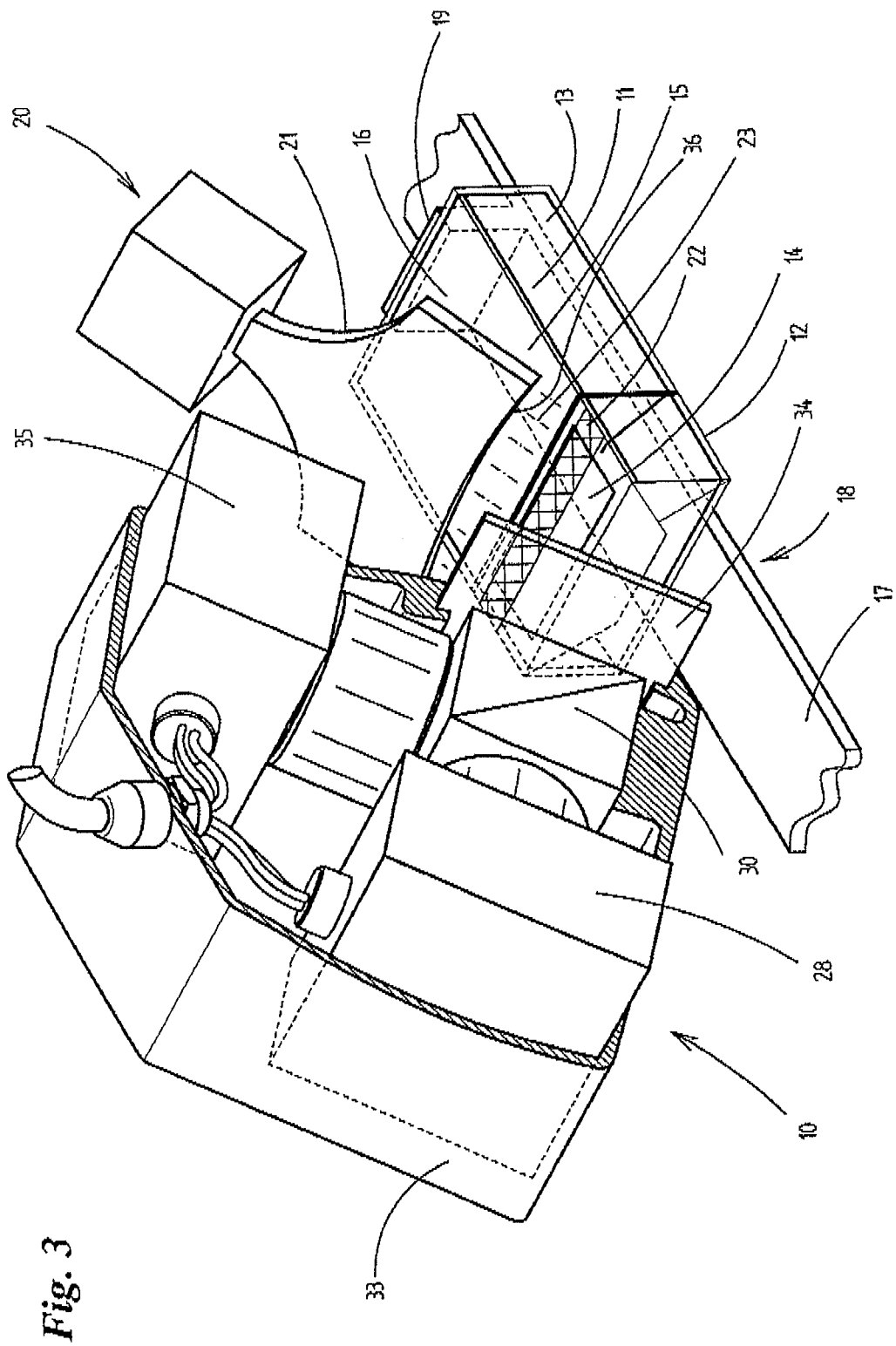
FIG. 3 shows the test device in FIG. 2 in partially sectioned perspective view.

FIGS. 2 and 3 illustrate an alternative embodiment of the test device 10.

The cameras 28, 35 and a beam splitter 30 (described in more detail below) with integrated polarization filters 31, 32 are arranged inside a housing 33. The reflected light beams 24, 25 enter the housing 33 after first passing through a protective glass 34 of the housing.

The beam splitter 30 with the polarization filters 31, 32 is arranged in the further beam path of the reflected beams 24, 25. The s-polarized beam 24 enters the beam splitter 30 and is deflected there completely by 90°. To this end, the beam splitter 30 interacts with the polarization filters 31, 32 such that only s-polarized light is deflected by 90° so that the camera 35 can record it. Only p-polarized light 25 can pass through the beam splitter 30 without deflection and be recorded by the camera 28.

It should be pointed out that of course not only the label 14 of the cigarette package 13 can be examined in this manner together with the film front side 16. Rather, any side of the film 12 and any side of the cigarette package 13 can be examined with the test device 10.

LIST OF REFERENCE NUMERALS 10 test device
11 product 12 film
13 cigarette package
14 label
15 front wall
16 film front side
17 conveying run
18 conveyor
10 pusher dog
20 illumination element
21 illumination body
22 section
23 light beam
24 light beam
24a partial light beam
24b partial light beam
25 light beam
25a partial light beam
25b partial light beam
26 beam splitter
27 polarization filter
28 camera
29 polarization filter
30 beam splitter
31 polarization filter
32 polarization filter
33 housing
34 protective glass
35 camera
36 concave surface

What is claimed is:

1. A method for testing moving products (11) having at least two layers, wherein at least one layer (14) of the product (11), which is arranged further inwards, namely an inner layer, is covered at least regionally by at least one, at least partially transparent product layer (16), which is arranged further outwards, namely an outer layer, comprising the steps of:
   a) illuminating the outer layer (16) of the product (11) by unpolarized light, with light that is reflected at the outer layer (16) comprising at least 70% of linearly s-polarized light;
   b) the s-polarized component of the light reflected by the outer layer (16) and/or of light reflected by the inner layer (14) and/or a p-polarized component of the light reflected by the outer layer (16) and/or of the light reflected by the inner layer (14) is/are recorded in each case separately using at least one suitable electrooptic recording element (28, 35) in the form of an image or partial image of the product (11),
   c) the recorded s-polarized and/or the recorded p-polarized light component is/are evaluated in order to be able to draw conclusions relating to features of the outer layer (16) and/or of the inner layer (14),
   wherein the outer layer (16) is part of a film wrap (12) of a cigarette package (13) and the inner layer (14) is part of the cigarette package (13), wherein the angle of incidence, under which the outer layer (16) is illuminated, is greater than 85% of the Brewster angle of the outer layer (16) and smaller than 115% of the Brewster angle of the outer layer (16), and approximately corresponds to the Brewster angle of the outer layer (16).

2. The method as claimed in claim 1, further comprising the step of, for examining the inner layer (14), evaluating the p-polarized light component of the reflected light, specifically the p-polarized image/partial image of the product (11).

3. The method as claimed in claim 2, wherein, for examining the outer layer (16) of the product (11), the evaluation comprises the subtraction of an image/partial image of the p-polarized light component from an image/partial image of the s-polarized light component.

4. The method as claimed in claim 1, wherein, for detecting defects in one or both layers (14, 16) of the product (11), s-polarized and/or p-polarized images/partial images of the product (11) is/are evaluated by detecting the defects by way of comparing stored reference images/reference partial images with the images/partial images of the product (11) recorded by the electrooptic recording element (28, 35) or by detecting the defects inside the images/partial images recorded by the electrooptic recording element (28, 35) using suitable pattern recognition methods.

5. The method as claimed in claim 1, wherein the s-polarized and/or the p-polarized light component is/are filtered out of the reflected light in each case using suitable polarization filters (27, 29, 31, 32).

6. The method as claimed in claim 1, wherein the products (11) are moved past the electrooptic recording element (28, 35) using a conveyor (18) during the testing process.

7. The method as claimed in claim 1, wherein the moving product is a package wrapped with film.

8. The method as claimed in claim 1, wherein the moving product is a cigarette package (13) wrapped with film.

9. The method as claimed in claim 1, wherein the light that is reflected at the outer layer (16) comprises at least 90% of linearly s-polarized light.

10. The method as claimed in claim 1, wherein the light that is reflected at the outer layer (16) comprises at least 95% of linearly s-polarized light.

11. A device for testing moving products (11) having an inner layer (14) covered at least regionally by at least one, at least partially transparent product outer layer (16), wherein the device has:
   at least one illumination element (20);
   a polarization filter (27, 31) for filtering p-polarized light and/or a polarization filter (29, 32) for filtering s-polarized light; and
   at least one electrooptic recording element (28, 35), wherein:
   a) the at least one illumination element (20) is directed at least at one side of the product (11) such that unpolarized light emitted by the illumination element (20) illuminates the outer layer (16) of the product (11), with light comprising at least 70%, of linearly s-polarized light,
   b) the polarization filter (27, 31) for filtering the p-polarized light and/or the polarization filter (29, 32) for filtering the s-polarized light is/are arranged in a beam path of the light reflected at the outer layer (16) and/or the inner layer (14),
   c) the at least one electrooptic recording element (28, 35) is positioned such that it records the s-polarized light and/or the p-polarized light after passage through the polarization filter(s) (27, 29, 31, 32) in each case separately as an image or partial image of the product, and
   d) the outer layer (16) is part of a film wrap (12) of a cigarette package (13) and the inner layer (14) is part of the cigarette package (13), wherein the angle of incidence, under which the outer layer (16) is illuminated, is greater than 85% of the Brewster angle of the outer layer (16) and smaller than 115% of the Brewster angle of the outer layer (16), and approximately corresponds to the Brewster angle of the outer layer (16).

12. The device as claimed in claim 11, further comprising an evaluation unit, which evaluates the images transmitted by the camera (28, 35), for detecting defects in the outer and/or inner layers (14, 16) of the product (11).

13. The device as claimed in claim 11, wherein the device has at least two electrooptic recording elements (28, 35), specifically a first electrooptic recording element (35) for recording the s-polarized light component of the reflected light and a second electrooptic recording element (28) for recording the p-polarized light component of the reflected light.

14. The device as claimed in claim 13, wherein the light reflected by the product is split into two partial beams using a beam splitter (26), wherein, for recording a first partial beam, the first electrooptic recording element (35) is positioned in a beam path of the first partial beam and the second electrooptic recording element (28) is positioned in a beam path of the second partial beam, wherein one of the polarization filter (27, 29) which blocks p-polarized light and transmits s-polarized light is arranged in the beam path of the first partial beam upstream of the first electrooptic recording element (35) and another of the polarization filters (27, 29) which blocks s-polarized light and transmits p-polarized light is arranged in the beam path of the second partial beam upstream of the second electrooptic recording element (28).

15. The device as claimed in claim 13, wherein the light reflected by the product is split into two partial beams using a beam splitter (30) and wherein the polarization filters (31, 32) are part of the beam splitter (30).

16. The device as claimed in claim 11, wherein the electrooptic recording element (28, 35) is configured in the form of a line-scan camera with a single sensor line.

17. The device as claimed in claim 11, wherein the illumination element (20) is configured and positioned such that it produces on the product (11) a strip-type illuminated area that is illuminated as uniformly as possible.

18. The device as claimed in claim 11, wherein the moving product is a package wrapped with film.

19. The device as claimed in claim 11, wherein the moving product is a cigarette package (13) wrapped with film.

20. The device as claimed in claim 11, wherein the light emitted by the illumination element (20) comprises at least 90% of linearly s-polarized light.

21. The device as claimed in claim 11, wherein the light emitted by the illumination element (20) comprises at least 95% of linearly s-polarized light.

* * * * *